US010350043B2

(12) United States Patent
Erikstrup (10) Patent No.: US 10,350,043 B2
(45) Date of Patent: Jul. 16, 2019

(54) URINE FLOW CONTROL DEVICE, SUCH AS AN INCONTINENCE DEVICE

(71) Applicant: MAGCATH APS, Frederiksberg C (DE)

(72) Inventor: Niels Erikstrup, Frederiksberg C (DK)

(73) Assignee: MAGCATH APS, Frederiksberg C (DK)

( * ) Notice: Subject to any disclaimer, the term of this patent is extended or adjusted under 35 U.S.C. 154(b) by 390 days.

(21) Appl. No.: 14/894,864

(22) PCT Filed: May 28, 2014

(86) PCT No.: PCT/DK2014/050150
§ 371 (c)(1),
(2) Date: Nov. 30, 2015

(87) PCT Pub. No.: WO2014/191002
PCT Pub. Date: Dec. 4, 2014

(65) Prior Publication Data
US 2016/0113749 A1  Apr. 28, 2016

(30) Foreign Application Priority Data
May 29, 2013 (EP) .................................. 13169775

(51) Int. Cl.
*A61F 2/00* (2006.01)
(52) U.S. Cl.
CPC .......... *A61F 2/0018* (2013.01); *A61F 2/0009* (2013.01)
(58) Field of Classification Search
CPC .... A61F 2/0004; A61F 2/0009; A61F 2/0022; A61F 2002/009; A61F 2002/0091; A61F 2/0018
See application file for complete search history.

(56) References Cited

U.S. PATENT DOCUMENTS

| 5,234,409 A | 8/1993 | Goldberg et al. |
| 5,246,445 A * | 9/1993 | Yachia ...................... A61F 2/88 604/104 |

(Continued)

FOREIGN PATENT DOCUMENTS

| EP | 0752251 | 1/1997 |
| WO | 95/34253 | 12/1995 |

(Continued)

OTHER PUBLICATIONS

International Search Report on corresponding PCT application (PCT/DK2014/050150) from International Searching Authority (EPO) dated Jul. 3, 2014.

(Continued)

*Primary Examiner* — Carrie R Dorna
(74) *Attorney, Agent, or Firm* — Klein, O'Neill & Singh, LLP (57) ABSTRACT

A urine flow control device, such as an incontinence device, for insertion into a urethra, device comprising: a body having a first end and an opposite second end and a middle part connecting the first end and the second end, a hollow chamber formed in the middle part allowing a mounting tool to extend from the first end to the second end, a fluid channel defined from the second end to the first end via the hollow chamber, a head part at the first end, the head part being integral with said body and comprising a chamber with a displaceable valve member and a valve seal surface, the head part formed so that when a mounting tool is positioned in the device the valve member is displaced inside the head part by the mounting tool and when the mounting tool is not in the device the valve member seals the valve seal surface so as to seal the fluid channel, the head part having an opening for receiving the mounting tool and for urine discharge, the second end being formed so that the distal end of the mounting tool elongates the body when inserted in the (Continued)

hollow chamber and applying an elongating force to the body.

25 Claims, 8 Drawing Sheets

(56) References Cited

U.S. PATENT DOCUMENTS

| | | | | |
|---|---|---|---|---|
| 5,476,434 | A | 12/1995 | Kalb et al. | |
| 5,704,926 | A * | 1/1998 | Sutton ................. | A61M 25/005 604/264 |
| 6,066,088 | A * | 5/2000 | Davis .................... | A61F 2/0022 128/DIG. 25 |
| 6,183,413 | B1 * | 2/2001 | Migachyov ........... | A61F 2/0022 600/29 |
| 6,213,936 | B1 * | 4/2001 | Nishioka ............... | A61F 2/0009 600/29 |
| 2002/0177902 | A1 * | 11/2002 | Rioux ....................... | A61F 2/04 623/23.67 |
| 2009/0157053 | A1 * | 6/2009 | Davis .................... | A61M 25/01 604/544 |

FOREIGN PATENT DOCUMENTS

| | | |
|---|---|---|
| WO | 97/39697 | 10/1997 |
| WO | 00/30560 | 6/2000 |

OTHER PUBLICATIONS

International Preliminary Report on Patentability on corresponding PCT application (PCT/DK2014/050150) from International Searching Authority (EPO) dated May 15, 2015.

* cited by examiner

URINE FLOW CONTROL DEVICE, SUCH AS AN INCONTINENCE DEVICE

CROSS-REFERENCE TO RELATED APPLICATIONS

This application is the national phase entry, under 35 U.S.C. Section 371(c), of International Application No. PCT/DK2014/050150, filed May 28, 2014, claiming priority from European Application No. 13169775.7, filed May 29, 2013. The disclosures of the International Application and the European Application from which this application claims priority are incorporated herein by reference in their entireties.

FEDERALLY SPONSORED RESEARCH OR DEVELOPMENT

Not Applicable

BACKGROUND

The present invention relates to a urine flow control device, such as an incontinence device.

Incontinence is the inability of any of the physical organs to restrain discharges of their contents; in the present context, incontinence is considered the involuntary discharge or evacuation of urine. This could e.g. be during movement, such as jumping, or when sneezing or laughing where persons suffering from incontinence experience problems.

Persons suffering from incontinence are often compelled to wear a pad for collecting urine being discharged from the urethra. In addition, persons suffering from incontinence may experience that the discharge of urine causes unwanted odours, which may cause the person to feel uncomfortable and embarrassed. Therefore, there is a need for a device hindering uncontrolled discharge of urine.

Some persons, on the other hand, have problems emptying their bladder. This may be due to low detrusor activity, which is associated to neurological or myogenic conditions. It may also be due to patient age factors, medication or bladder outlet obstruction. Such patients insert catheters when emptying the bladder. Either they catheterize themselves, have nurses perform the catheterization, or they carry a catheter permanently.

Such patients may be helped by wearing a valve catheter, as this can eliminate the need for catheterization every time the bladder needs emptying.

U.S. Pat. No. 5,476,434 discloses an incontinence device with an insertion/mounting tool and having in one embodiment a duck bill valve, which by its nature opens and reopens readily through sideways bending of the flat rubber lips defining the valve opening. In another embodiment a ball valve is used; the ball valve is part of a plug inserted into the device after it has been placed in the urethra by the insertion/mounting tool, and the ball is configured to be attracted by a magnetic disc. The ball is displaced along the length of the device by a spring upon removal of the magnet.

It is an object of the present invention to provide an alternative to the prior art whereby reinsertion, using the insertion/mounting tool, of the catheter once removed is made difficult. Such reuse may cause urinary tract infections. The mounting tool may preferably be in the form of a pin, such as a generally cylindrical cross-section pin, movable within the device along a path, which normally is along a central axis of the device.

Another object is to provide a catheter offering an improved usability and comfort.

The above described object and several other objects are intended to be obtained in a first aspect of the invention by providing a urine flow control device, such as an incontinence device, for insertion into a urethra, device comprising: a body having a first end and an opposite second end and a middle part connecting the first end and the second end, a hollow chamber formed in the middle part allowing a mounting tool to extend from the first end to the second end, a fluid channel defined from the second end to the first end via the hollow chamber, a head part at the first end, the head part being integral with said body and comprising a chamber with a displaceable valve member and a valve seal surface, the head part formed so that when a mounting tool is positioned in the device the valve member is displaced inside the head part by the mounting tool and when the mounting tool is not in the device the valve member seals the valve seal surface so as to seal the fluid channel, the head part having an opening for receiving the mounting tool and for urine discharge, the second end being formed so that the distal end of the mounting tool elongates the body when inserted in the hollow chamber and applying an elongating force to the body.

Further embodiments are defined in the dependent claims.

In one embodiment there is provided a urine flow control device, such as an incontinence device, for insertion into a urethra, the device comprising: a body having a first end and an opposite second end and a middle part connecting the first end and the second end, a hollow chamber formed in the middle part allowing a mounting tool to extend from the first end to the second end, the first end having an opening for receiving the mounting tool, the second end being formed so that the body elongates when the mounting tool is inserted in the hollow chamber and applies a force to the second end, a head part at the opening of the first end, the head part comprising a chamber, a valve sealing surface and a valve member, the head part formed so that when the mounting tool is inserted into the device the valve member is displaced from the valve sealing surface and when the mounting tool is not inserted into the device the valve member is in a resting position where the head part abuts the valve member so that the valve member hinders flow.

In yet another embodiment there is provided a urine flow control device, such as an incontinence device, for insertion into a urethra, the device comprising: a body having a first end and an opposite second end and a middle part connecting the first end and the second end, a hollow chamber formed in the middle part allowing a mounting tool to extend from the first end to the second end, a fluid channel defined from the second end to the first end via the hollow chamber, a head part at the first end, the head part comprising a chamber and a valve member and a valve seal surface, a tab formed on the outside of the head so that when the tab is pulled by a user the valve member is displaced inside the head part and when the tab is released the valve member seals the valve seal surface so as to seal the fluid channel.

It is an advantage to provide a device the operation of which is as easy as possible for the user. Devices or plugs that have to be completely removed from the urethra in order to open for urine flow are inconvenient. It is better to have a device that can stay for several days in the urethra once mounted. In this case, a valve is needed in the device. Such a valve must be easy to open and close. It is especially advantageous if the valve closes automatically once the user decides not to provide the means that opens the valve.

It is further an advantage to provide a location of the valve that prevents the entrance of contaminations e.g. hair to the sealing surfaces.

It is further an advantage to provide a device that is difficult to reinsert in the urethra, once it is removed therefrom. This prevents reuse and the potential introduction of bacteria into the urethra. In the present invention, this is ensured by delivering a package with the device having a mounting tool inserted. This mounting tool is mandatory for the insertion of the device. Once the device is inserted, the mounting tool is withdrawn and removed from the device. The withdrawal of the mounting tool allows the valve member to move into the position where it seals against the valve sealing surface. In addition to this, the valve member blocks for any re-insertion of the mounting tool. This prevents or at least hinders the re-use of the device.

It is further an advantage to provide a device where the valve can be opened without touching the device. This is especially beneficial in cases where the user needs the assistance from a nurse or other persons in order to open the valve. This provides a better comfort and is less intimidating for the user as well as more hygienic in general.

Advantageously the valve member may have permanent magnetic properties. This will e.g. allow a user move the valve member away from the sealing surface and open the valve by placing a magnetic material or a magnet close to the device. Thus, the urine flow control device may be used with an external device providing magnetic attraction to the valve member so that the valve member is displaced from the resting position thereby allowing fluid to flow through the opening.

By magnet is meant a material that generates a magnetic field, and by magnetic is meant a material that is attracted by a magnet.

The device may easily be inserted in a urethra by the user herself and she can herself exchange or replace the device when needed. The mounting tool eases the mounting procedure as the mounting tool extends the length of the device whereby the outer diameter of the device is reduced. This promotes mounting, and further allows the diameter of the device to be designed for maximum retention force when mounted in the urethra.

In an embodiment, the valve member is not a magnet in itself, but may be magnetic and thereby moved by an external magnet so as to allow urine to pass through the device, meaning that the valve member may be made fully or partially from a magnetic material.

Advantageously the body of the device may have a tapering outer geometry so as to provide a surface abutting the inner wall of the urethra for a substantial part of the body of the device. This makes the device more prone to move towards the bladder, when mounted in a urethra, than to fall out, e.g. while the user is walking. The head of the device ensures that the device does not move longer into the bladder than intended.

Advantageously a magnetic part may be located between the valve member and the second end of the body. This provides an increased mechanical stability to the area there the valve member abuts the opening and may also provide a force between the valve member and the metal part if the valve member is a magnet.

The second end may comprise a protrusion for engaging a wall of a bladder or the innermost part of the urethra where this widens into the bladder. This increases the force needed to retract the device from the urethra, and thereby reduces the risk for unintended loss of the device.

When the mounting tool is inserted into the flow control device it is an advantage that it extends the length of the body when pushed towards the second end. This extension reduces the maximum diameter, or at least the diameter at certain places or regions of the device.

The valve member may be spherical, but other geometries may be used. One advantage of using a spherical or ball-shaped geometry is that the valve member can seal a circular opening independent of the orientation of the valve member. A further advantage is that a polished ball shape can easily be moved by the silicones elasticity or a magnetic force, as this shape has no edges that can hinder the movement to and from the sealing surface.

Advantageously a rigid, preferably metal, member may be embedded in the body at the first end so that the opening maintains a specific geometry when abutted by the valve member. The specific geometry may be circular, which is especially advantageous when the valve member is spherical as discussed above. In addition, a non-metal rigid member may be useful, as this too can ensure a circular sealing surface.

Both for production reasons, but also for the mechanical strength of the device and security and comfort of the user, the body of the device may be formed in one single piece, e.g. by silicone injection moulding. This also reduces the risk of parts falling off or dismantling while the device is in use.

For increased comfort for the user, the flexible parts of the device may be formed from silicone or polyurethane, or other biocompatible materials.

The device may comprise the head part having a tap positioned so that when the device is located in a urethra and the tab is pulled, the head part is moved so that the force that presses the valve member against the valve sealing surface is reduced, whereby the urine pressure can open the valve and urine can flow. Furthermore, the head will pivot so that the resulting urine flow will leave the orifice in a direction so that it does not come in contact with the fingers of the user. This further allows a user to discharge urine without being in possession of any tools. The tab may also be used in conjunction with an external device that applies a force to the valve member and further opens the valve for an increased flow of urine.

By pulling even harder in the tabs, the device is elongated or extended and the wide part of the device is forced to reduce its diameter, so that the device can pulled out of the urethra without the need for any tools. Medical grade silicone has sufficient strength for a safe operation.

The head part of the flow control device ensures that the first end of the body stays at the external wall of the urethra so that the entire device cannot enter the urethra. The shape and varying width along the length of the device ensures that it fits into the urethra so that no urine can pass between the device and the inner wall of the urethra. The tapered outer shape and the wide bulb ensure that the device stays in place once it is mounted.

Advantageously a coating may be applied to the outer surface of the device. The coating may be a bacteria reducing agent so as to reduce the risk of urinary tract infection. The coating may further have friction reducing properties for an eased mounting and withdrawal of the device from the urethra.

Advantageously the valve member may comprise a coating layer for reducing corrosion of the valve member and/or for reducing deposits and/or for improving cleaning and/or for improving biocompatibility.

A second aspect of the present invention relates to a package comprising a device according to the first aspect and a magnetic device or tool for opening the valve. This allows a user to easily obtain a complete package from e.g. a pharmacy or the like without having the trouble of locating a suitable tool, i.e. something with sufficient magnetic attraction to open the valve.

A package may be provided wherein a mounting tool is inserted into the device. As described elsewhere the operation of entering a mounting tool into a device according to the present invention is difficult and should not be performed by the user herself. By provided a mounting tool inserted into the urine flow control device in a package the user will be able to easily insert the device into the urethra.

The package may further comprise a lubricant for application to the device. This is an advantage to the user when applying the device to the urethra and ensures that a suitable medical grade lubricant is used.

The surface of the device may further be pre-lubricated so that it is ready for use and insertion upon opening the package and the user thereby does not have to apply the lubricant herself or risk that the lubricant and device are in some way incompatible.

This lubricant may further contain a mild sedative that makes the mounting of and adaptation to the device more comfortable for the user.

The package may further comprise an anti-bacterial agent in a container. This may be applied so as to reduce the risk of urinary tract infection.

The first and second aspect of the present invention may each be combined with any of the other aspects. These and other aspects of the invention will be apparent from and elucidated with reference to the embodiments described hereinafter.

BRIEF DESCRIPTION OF THE FIGURES

The device according to the invention will now be described in more detail with regard to the accompanying figures. The figures show some ways of implementing the present invention and are not to be construed as being limiting to other possible embodiments falling within the scope of the attached claim set.

DETAILED DESCRIPTION OF AN EMBODIMENT

It is emphasized that the urine flow control device discussed in the following may equally be used by a person suffering from problems emptying their bladder. For convenience, however, the urine flow control device of the invention will in the following be described in the context of incontinence devices.

Figure 1:
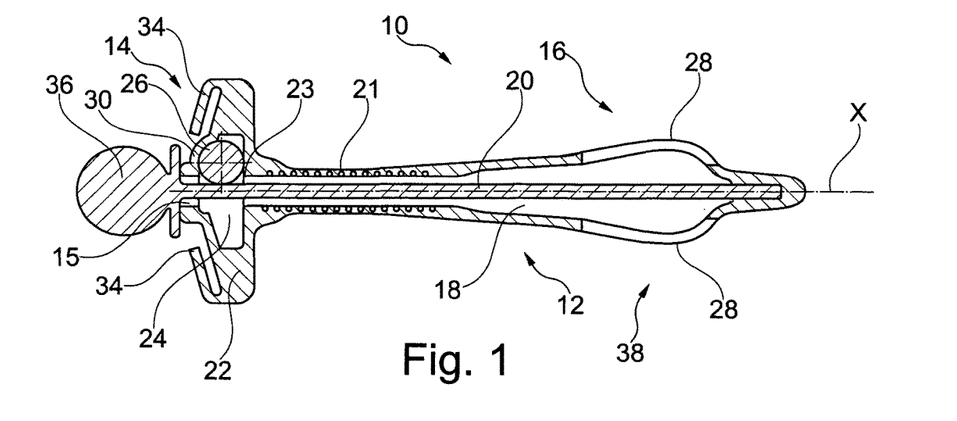
FIGS. 1-5 are schematic illustrations of flow control devices where a mounting tool is inserted and forces the device to elongate, whereby the device further has a temporary reduced diameter due to this elongation.

FIG. 1 is a schematic view of a urine flow control device of an embodiment of the invention, for insertion into a urethra as an incontinence device 10. The device 10 comprises a body 12 having a first end 14, an opposite second end 16 and a middle part 13 connecting the first end 14 and the second end 16. Preferably, the body 12 with the first end 14 and the second end 16 is integrally molded of a soft flexible material, such as silicone, while internal parts or elements may be of eg. metal. The body extends along a longitudinal axis X of the device 10; in the shown embodiment the axis X is straight.

A hollow chamber 18 is formed in the body 12 allowing a removable mounting tool 20, such as in the form of an elongated pin to extend from the first end 14 to the second end 16. The tool 20 has a proximal end with a tool head 36 and a distal end, and is inserted into the hollow chamber 18 through an opening 15 at the first end 14 of the device 10. The second end 16 of the device is formed or shaped so that the distal end of the mounting tool 20 cannot extend outside the body 12 when the mounting tool 20 is inserted in the hollow chamber 18. The mounting tool is movable along the axis X which defines a path of movement of the tool relative to the body 12.

The device 10 is preferably delivered to the user with the tool 20 installed partially. The mounting tool 20 may be of plastic or metal and is configured to abut against the inner side of the device 10 at the second end 16. This allows the mounting tool 20 to force the body 12 to elongate or extend, such as by deformation of the middle part 13, and thereby become narrower for easing the insertion of the device into the urethra. The user applies a manual force to the tool head 36 to fully install the tool 20, i.e. to thereby move it fully into the body 12 so as to give rise to the aforementioned extension, against inherent forces resisting the deformation of the device 10. Preferably, the second end 16 is molded with a well W (see also FIG. 6) which receives the distal end of the tool 20 and which has a bottom end against which the distal end of the tool 20 applies a force to extend the device body 12. It will be understood that the aforementioned force is applied as a person inserts the tool 20 fully into the device 10, such as until the tool head 36 bears against the first end 14 of the device 10. The well W is a relatively narrow constriction.

As shown, at the first end 14, a head part 22 is integral with the body 12 at the opening 15. The head part 22 comprises a chamber 24 and a valve member 26. The valve member may in some embodiments be displaceable from its first, resting (i.e. sealing) position under the influence of a magnetic field. The valve member 26 is preferably a magnet, but may be made from a magnetic material and may comprise non-magnetic material, e.g. a coating or a core or layer of different material.

Figure 6:
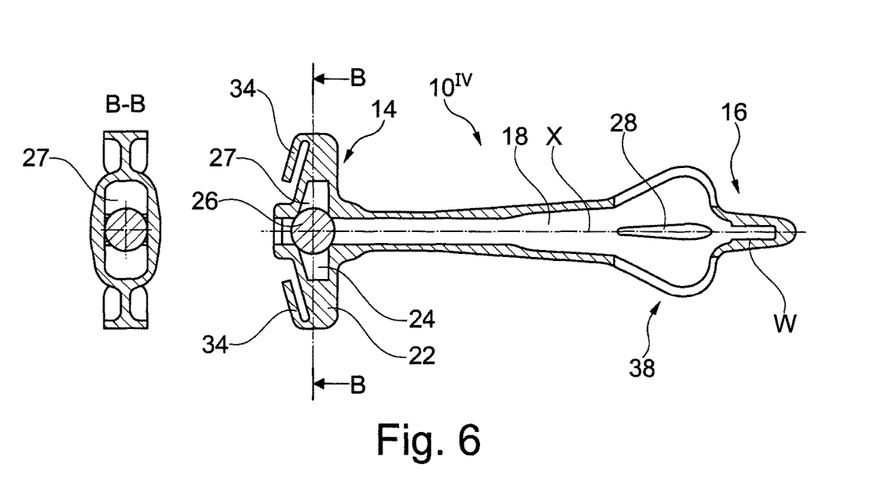
FIG. 6 is a schematic illustration of the device of FIG. 5, where the mounting tool has been removed so that the device has shortened and the bulb has expanded to a larger diameter.
Figure 7:
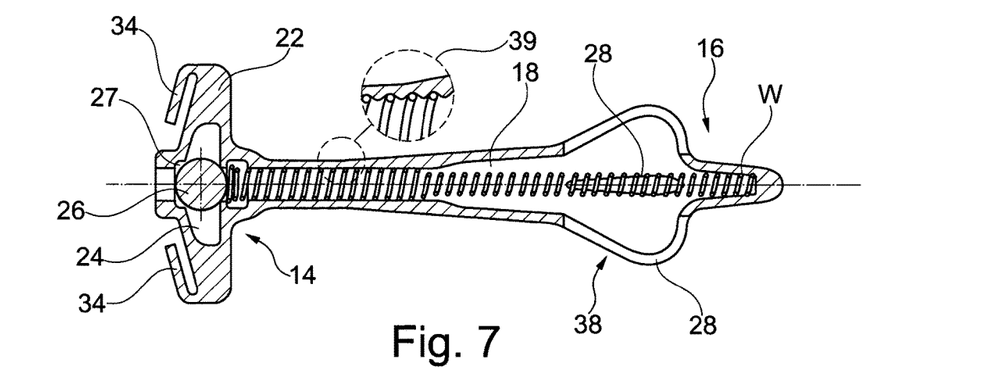
FIG. 7 is a schematic illustration of a device without a mounting tool inserted, where a spring extends throughout the length of the device.

In the shown embodiments the head part 22 is mechanically flexible and formed so that when the mounting tool 20 is positioned in the incontinence device 10, i.e. received in the hollow chamber 18, the valve member 26 is displaced sideways relative to the valve sealing surface 23 (where the valve member 26 is a ball, the sideways displacement will typically be in the order of 0.3-0.7, such as in the order of 0.5, times the diameter of the ball, to allow for such a sideways displacement that there the tool 20 can be accommodated) and when the mounting tool 20 is not in the incontinence device, i.e. removed from the hollow chamber 18 as e.g. illustrated in FIGS. 6 and 7, the valve member 26 automatically, due to a combination of push from the deformed elastic body and magnetic attraction between the valve member 26 and metal (to be discussed below) located on the opposite side of the seal, returns to a resting position where the head part 22 abuts the valve member 26 so that the valve member 26 seals the valve sealing surface 23 and closes for flow. Further when an external device (to be discussed further below) applies a magnetic force to the valve member 26, that is larger than the force between the valve member 26 and the aforementioned metal located behind the valve, the valve member 26 is displaced from the valve sealing surface 23 thereby allowing fluid to flow through the opening. In the present context, the resting position is meant to describe a first position wherein the valve member is positioned so that a seal is formed between the valve sealing surface and the valve member.

This could be obtained as a result of no mounting tool being inserted into the device or any external magnetic force being applied, and the resting position is mainly obtained as a result of the mechanical forces of the head part and valve sealing surface onto the valve member.

Figure 2:
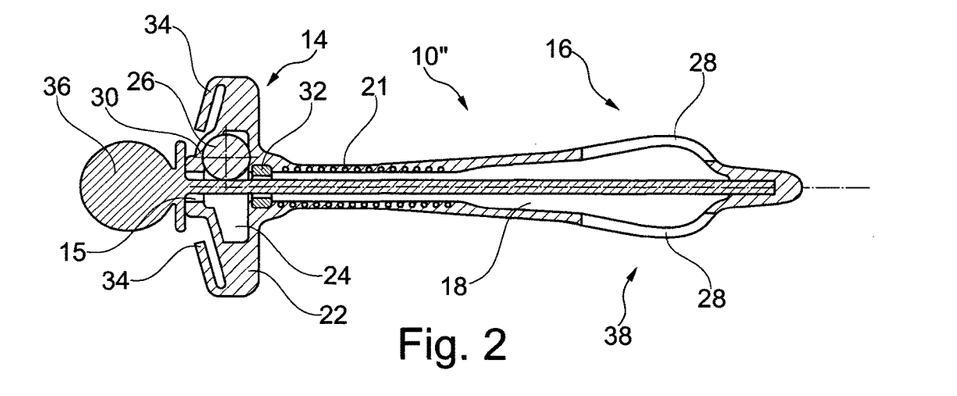
Figure 3:
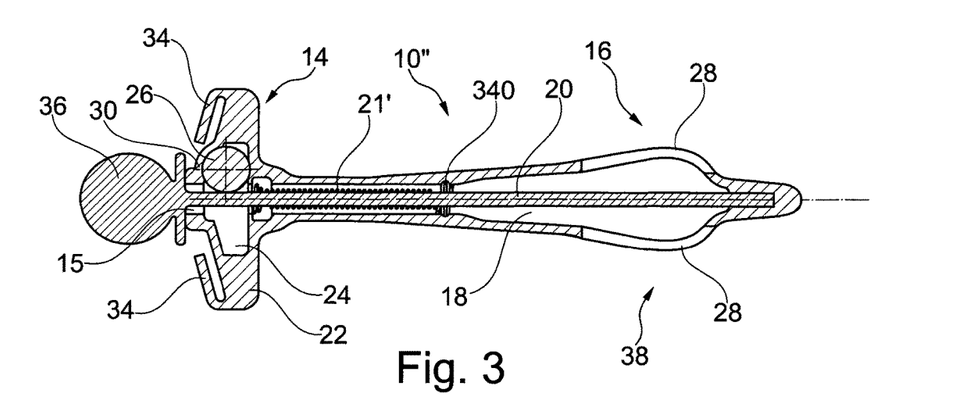
Figure 4:
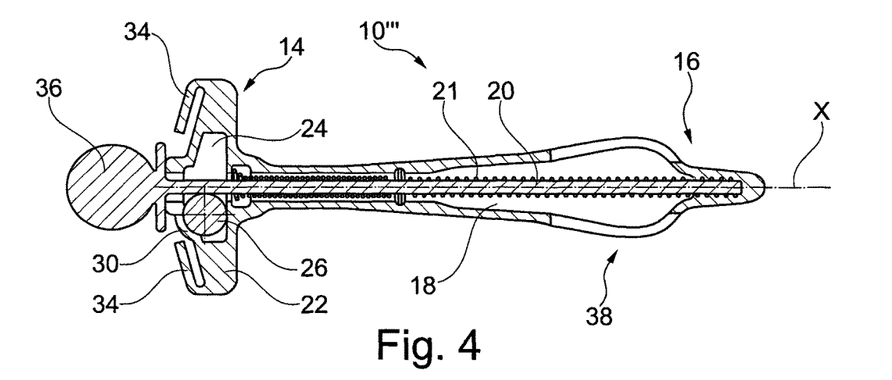
Figure 5:
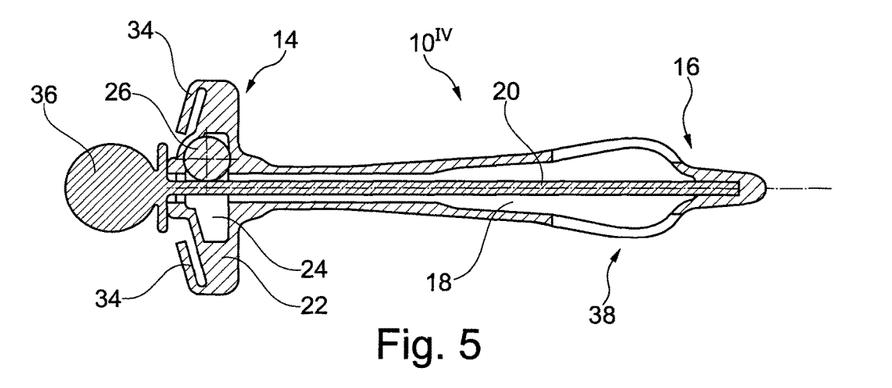

In FIGS. 1 and 2 a helical metal coil in the form of a spring 21 is embedded in the body 12 in the part nearest the first end. The helical metal coil provides mechanical stability and provides a guard against kinking, i.e. the unintended collapse of the wall and unintended blocking of flow so that the internal flow path stays open. In FIG. 3 on the other hand, the helical metal coil 21' extends inside the hollow chamber 18, between the first part 14 and a fixture 340. In FIGS. 1-3 it is not illustrated that the spring extends the entire length between the first part 14 and the second part 16, this may be seen e.g. in FIG. 4. The helical coil further provides material to create a magnetic attraction force to the valve member 26, if the valve member is a magnet.

The head part 22 is designed in a combination of thickness and material flexibility/elasticity sufficient to allow the valve member 26 to move by a combination of elasticity and magnetic force into its first position where the valve is sealed, while having enough flexibility and space for movement to allow the valve member 26 to be temporarily displaced to its second position relative to the valve sealing surface and thereby allowing urine to pass.

The second end 16 is intended to extend into the part of the urethra where it widens into the bladder of a user, as is illustrated e.g. in FIG. 6. Openings 28 are formed at the second end 16 so as to allow urine to flow from the bladder through the hollow chamber 18 and further through the opening at the first end 14 as long as the valve member 26 is not positioned to seal the valve sealing surface. The magnetic attraction between the valve member 26 and metal on the opposite side of the valve sealing surface will hold the valve member 26 in the intended position when no external magnetic force is applied to the valve member 26. This is also illustrated in FIG. 6 and discussed below. Preferably, there is a small clearance 27, see FIGS. 6 and 7 between the wall and the valve member 26 when it is the position where it seals against the valve sealing surface. This allows the valve member 26 to move and dislodge from the valve sealing surface 23 when an external magnetic force is applied.

FIG. 2 is a schematic illustration of an incontinence device 10' in many ways similar to the device illustrated in FIG. 1. In the incontinence device 10' a metal ring 32 has been embedded at the first end 14. Other geometries than ring or toroid may be used. It is presently preferred that a ring or toroid shape is used for a supporting member embedded as described while a ball or sphere shaped valve member is used, as this provides the most accommodating and easy-to-use configuration with reduced risk of leaks. Other materials may be used for the ring as one goal is to provide increased mechanical stability to the area and thus non-metallic materials may be used, e.g. ceramic or plastic materials. A metal ring gives the potential for a stronger magnetic force and thereby a more secure seal which might be required for some patients. Further, the valve sealing surface where the moveable closure device 26 and the metal ring 32 meet have increased mechanical stability and is geometrically more well defined so that it maintains the preferred geometry of the valve sealing surface, compared to the embodiment in FIG. 1, e.g. ensuring a circular geometry that fits a spherically shaped valve member.

When using the device as illustrated in FIG. 1 the user has the option to pull the tab 34 and deform the head part in order to increase the distance between the valve member 26 and the metal, such as the helical coil 21, 21', on the other side of the valve sealing surface so as to reduce the magnetic force between the two, to a level where the internal pressure from the urine can open the valve and thereby allowing urine to pass out of the device.

When using the device as illustrated in FIG. 6 the user has the option to pull the tab 34 in order to alter the geometry of the chamber 24 so that the elastic forces that hold the valve member pressed against the valve sealing surface 23 are reduced so that the urine pressure can force the valve to open whereby the urine can flow. Once the tab 34 is released, the elasticity of the device forces the valve member back to the valve-sealing surface so that the valve is closed.

In FIG. 3, a part of the spring has an increased coil diameter 340. The length with increased diameter 340 provides increased retention force for keeping the spring 21' in place, especially if the body has a corresponding recess that holds the spring into a well-defined place. In this embodiment the elongation and contraction of the wide part or bulb of the device is controlled by the stiffness and geometry of the bulb. The magnetic attraction and thus the sealing force is controlled by the strength of the magnet, the distance between the magnet and the metal on the other side of the valve seat and the geometry of this metal. An easy way is therefore to trim the force by changing the pitch and diameter of the helical coil as well as trimming the wire diameter and alloy of the coil. This allows variants of this device to be adjusted for different users.

FIGS. 6 and 7 schematically illustrate an incontinence device where the mounting tool 20, as illustrated in FIGS. 1-5, has been removed. The walls of the head part 22 abut the valve member 26 so that a seal is created at the opening so that urine may not pass through the device. Thereby the user will not leak urine unintentionally when the device is positioned in a urethra. In FIG. 7, the helical coil extends substantially throughout the length of the device and is received within the aforementioned well W, and preferably fixed thereto, such as by gluing, or in the process of molding the well W, whereas in FIG. 8 the helical coil extends substantially halfway through the length of the device.

Figure 15:
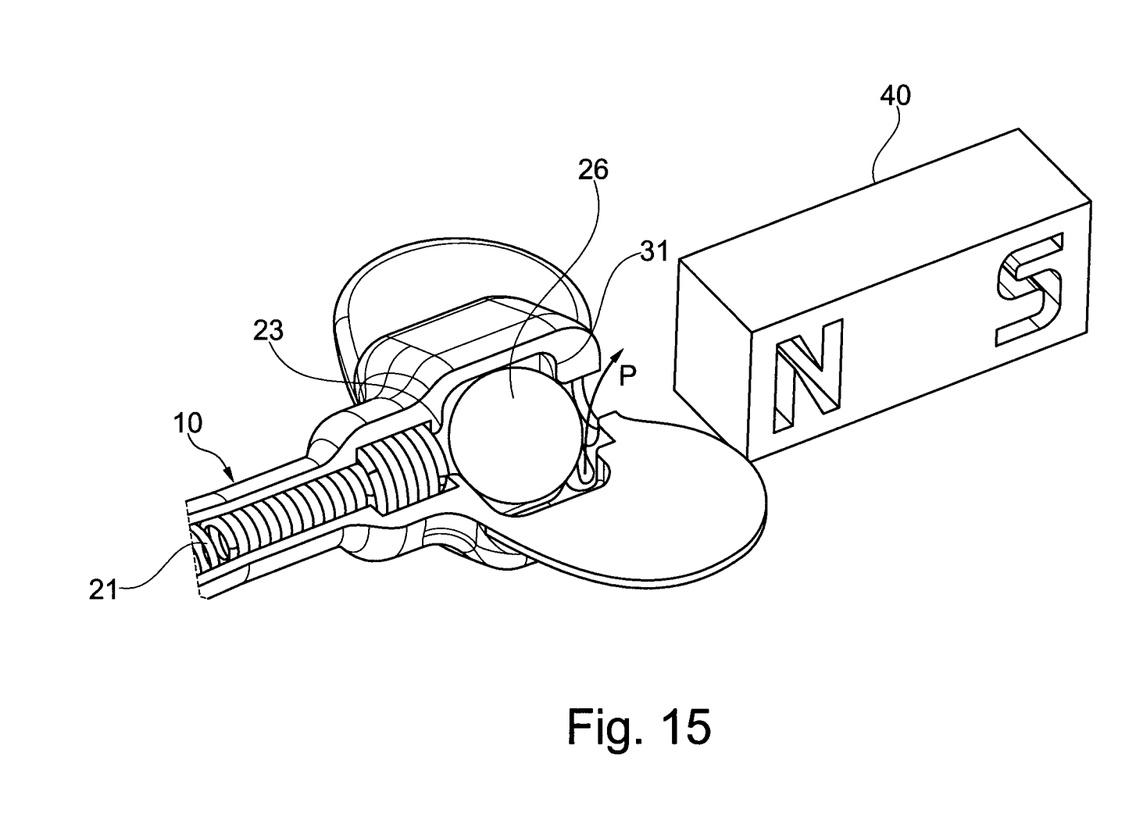
FIGS. 15-17 are perspective views showing details of further embodiments.

FIG. 7 illustrates an embodiment where the coil outer diameter is larger than the inner diameter of the device body in a part of the body closest to the valve member 26. In the circle 39 is illustrated a zoomed view of a part of the helical coil where it is seen that the coil outer diameter is larger than the inner diameter of the device body, i.e. the inner diameter of the hollow chamber. This ensures a squeezing of the coil so that it stays in a fixed place inside the device. This leaves one end of the coil in communication with the bulb, so that the bulb stiffness is partly controlled by this end of the coil. The location of the coil may further be secured by e.g. gluing or welding, so that not only a squeezing from the body is relied upon. The coil/spring 21 may have an increased pitch away from the valve member, as shown in FIG. 15, to reduce flow resistance in relation to urine flowing inside the coil towards the opening 15.

FIG. 6 schematically illustrates a device 10IV without a spring or helical coil.

It can be seen in FIG. 6 how the valve member 26 blocks for any reinsertion of the mounting tool 20. This prevents any reuse of the device, once it is removed from the urethra, thereby preventing use that may cause urinary tract infection. All of the illustrations show devices that have this property. A skilled person will be able to reinsert or insert a mounting tool, but the majority of users will not.

Figure 8:
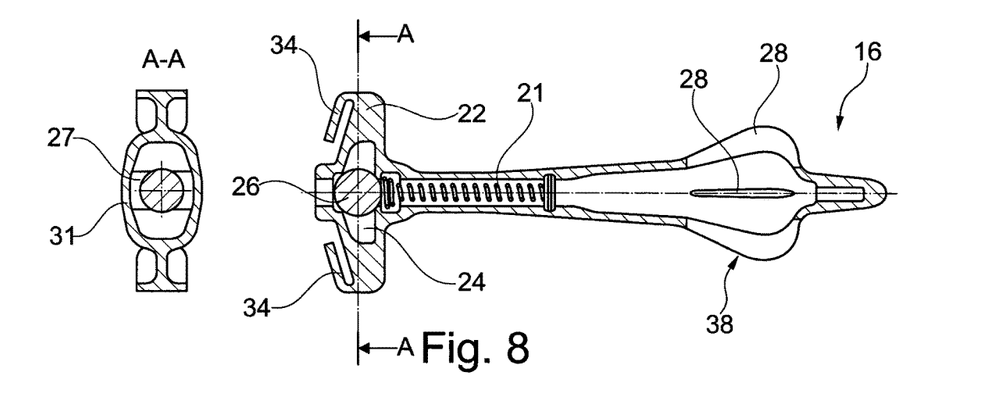
FIG. 8 is a schematic illustration of a device without a mounting tool inserted, where a spring extends partly through the length of the device and is held in place by inner grooves in the device, the wall of the bulb is somewhat thicker in this embodiment, illustrating a way to change the mechanical properties of the device.

In FIG. 8, the diameter of the coil widens at the end of the coil. This widened part of the coil fits into the aforementioned well W of the device, which ensures a well-defined location of the helical coil in the device body 12. This figure also shows that the thickness of the bulb 38 wall may be varied in order to provide a suitable stiffness of the bulb 38.

FIG. 8 further illustrates that the valve member 26 can only create a seal so that flow of urine is not possible if the valve member 26 is in contact with the valve sealing surface, at all other positions of the valve member 26 there will be some route or passage P along which urine will be able to flow out of the device, see also FIG. 15. For example if the valve member 26 abuts the surface at 31 it will not create a seal as this surface 31 does not have a geometry allowing a seal to be created.

FIGS. 6 and 8 further illustrate views along the lines B-B and A-A respectively. In these views, it may be seen how the valve member 26 is positioned over the valve sealing surface. When the device is mounted, pulling the tab 34 or applying a magnet or magnetic material as discussed above the valve member is temporarily moved so as to establish a flow of urine from the bladder. When external loads or forces are removed, e.g. the tab 34 is released, the head part 22 returns substantially to the resting position as illustrated in these figures.

Figure 9:
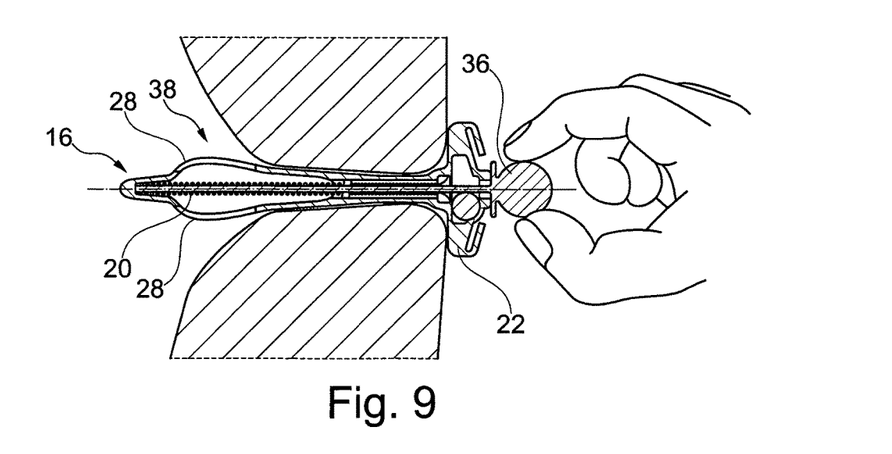
FIG. 9 is a schematic illustration of a device positioned in a urethra.
Figure 10:
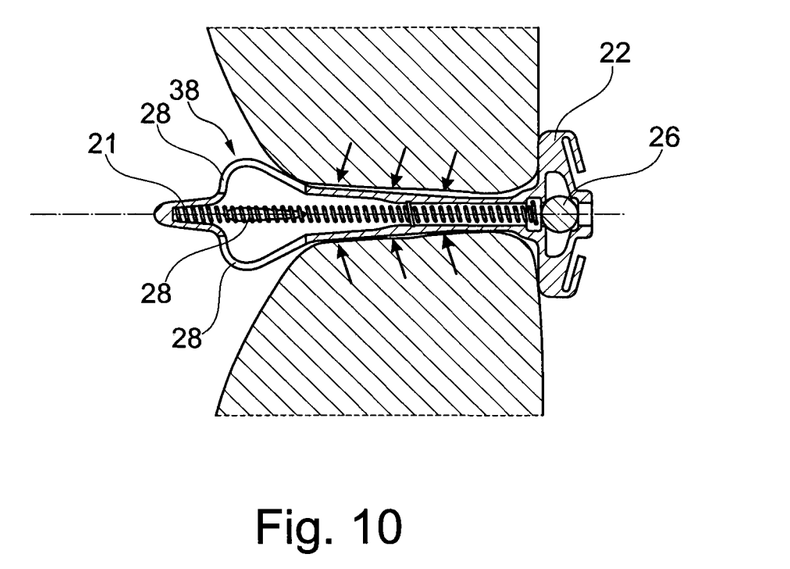
FIG. 10 is a schematic illustration of a device positioned in a urethra after the mounting tool has been removed.

FIG. 9 schematically illustrates an incontinence device being mounted in the urethra by a user, illustrated by the hand. The user has pushed the device into the urethra using the enlarged head of the mounting tool 20, which preferably has been partially or fully inserted into the device 10 already at factory level. The enlarged head ensures that the user cannot push or elongate the tool too far into the device, especially ensuring that the mounting tool does not extend freely into the bladder, further the enlarged head provides a good grip for the user. In an alternative embodiment the mounting tool includes a part having geometry in the shape of a shoulder, flange or other widening that ensures that the user cannot push the tool too far into the device, thereby preventing damage to the device. The mounting tool abuts the second end of the device so that the device is elongated in the process and thus is easier to press into the urethra. A lubricant may be added. The lubricant may further be accompanied by an anti-bacterial agent. When the device has been inserted and positioned correctly, the user retracts the mounting tool 20 from the device and by means of forces from the deformed head part and magnetic attraction the valve member 26 moves to and enters a position substantially as illustrated in FIG. 10 so that the valve closes and no urine is released unintentionally. The force from the spring 21 contracts the device so that a larger bulb 38 is formed at the second end 16 so that the device does not fall out of the urethra, i.e. stays in place, during use. The tapered or slightly conical outer shape of the body also contributes to retaining the device in place.

Figure 11:
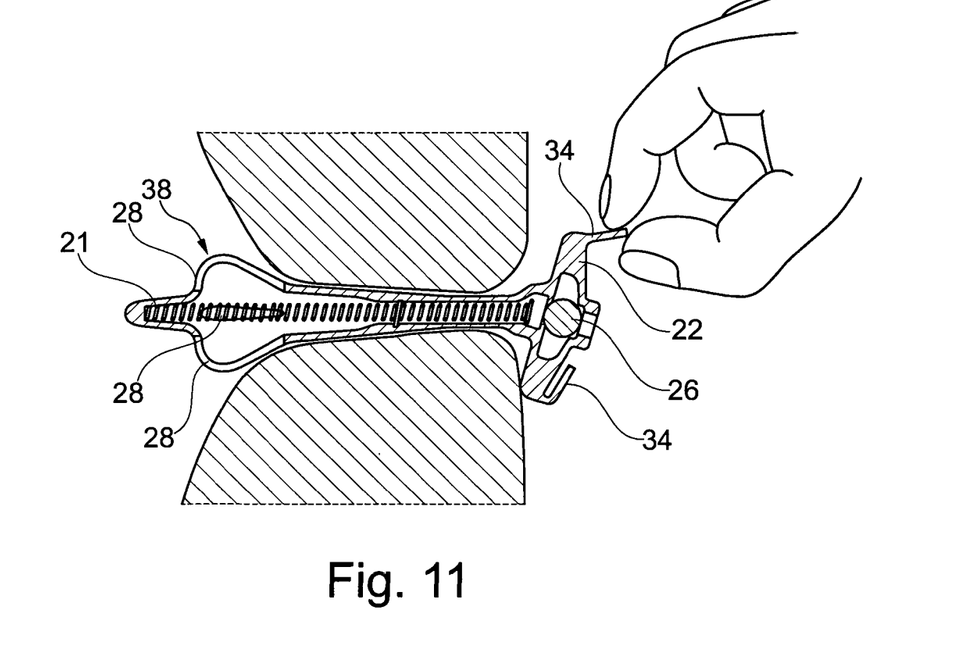
FIGS. 11 and 12 are schematic illustrations of a device being opened so as to discharge urine.

FIG. 11 schematically illustrates a situation where a user wishes to discharge urine by pulling one of the tabs 34. When the user pulls the tab 34, a small deformation in the material abutting the valve member 26 occurs and thereby the distance between the valve member 26 and the magnetic material in the other side of the valve sealing surface increases, so that the valve closure force is reduced to a level where the pressure exerted by the urine in the bladder will displace and open the valve so that urine can flow through the device. When the tab is released the valve member is returned to a position where the magnetic force can close the valve and hinder further flow. The devices illustrated in FIGS. 1-5 may all be operated in this manner.

Figure 12:
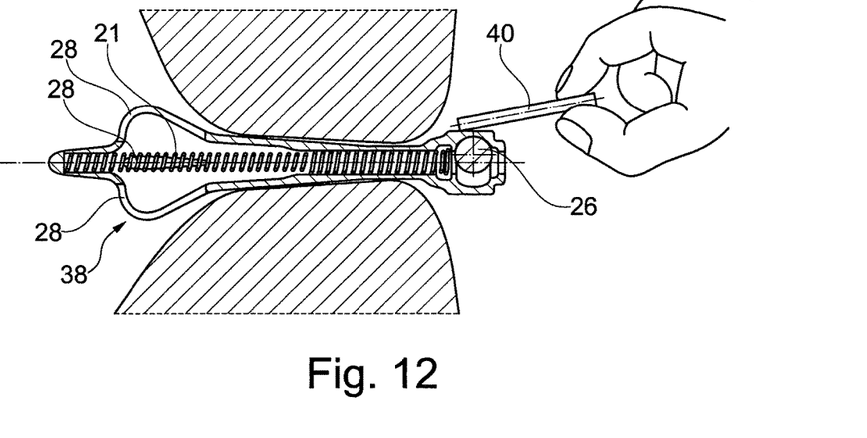

FIG. 12 schematically illustrates the situation where a user wishes to discharge urine by holding an external magnetic material 40, e.g. a ferromagnetic material, close to the device so that the magnetic force between the valve member and the external magnetic device moves the valve member 26 and opens the valve. When the user removes the external magnetic device sufficiently far away the valve member is automatically returned by the push from the deformed head part 22 and/or the pull from the magnetic attraction to the magnetic material in the device to recreate the seal as illustrated in FIG. 8. There is preferably a small distance, preferably in the range of 0.2-2 mm, between the valve member and the inner wall of the device. In presently preferred embodiments the diameter of the valve member is in the range 2-10 mm. Advantageously the valve member may be a Neobdynium magnet, and may have a coating of e.g. gold, but it should be clear that also other types of magnet materials will work fine.

Figure 13:
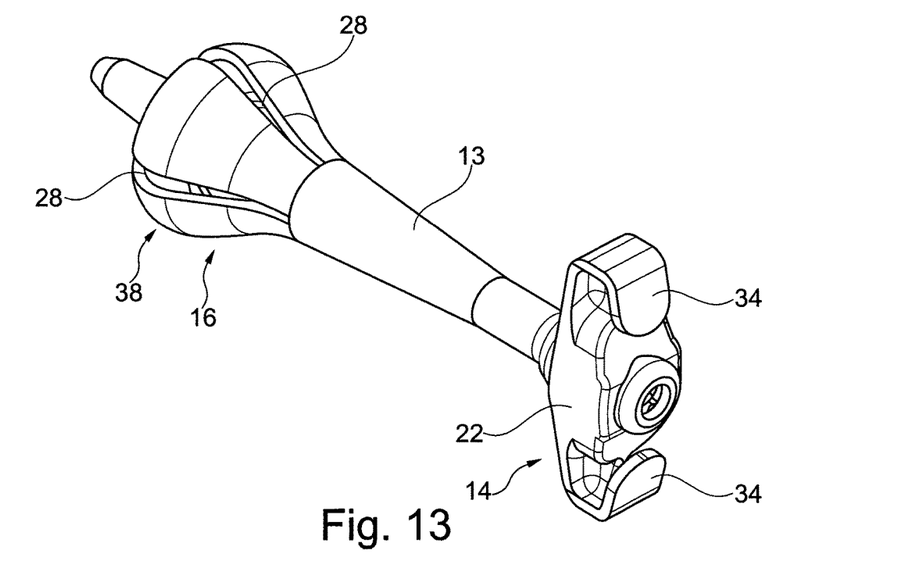
FIGS. 13 and 14 are schematic perspective illustrations of a device.
Figure 14:
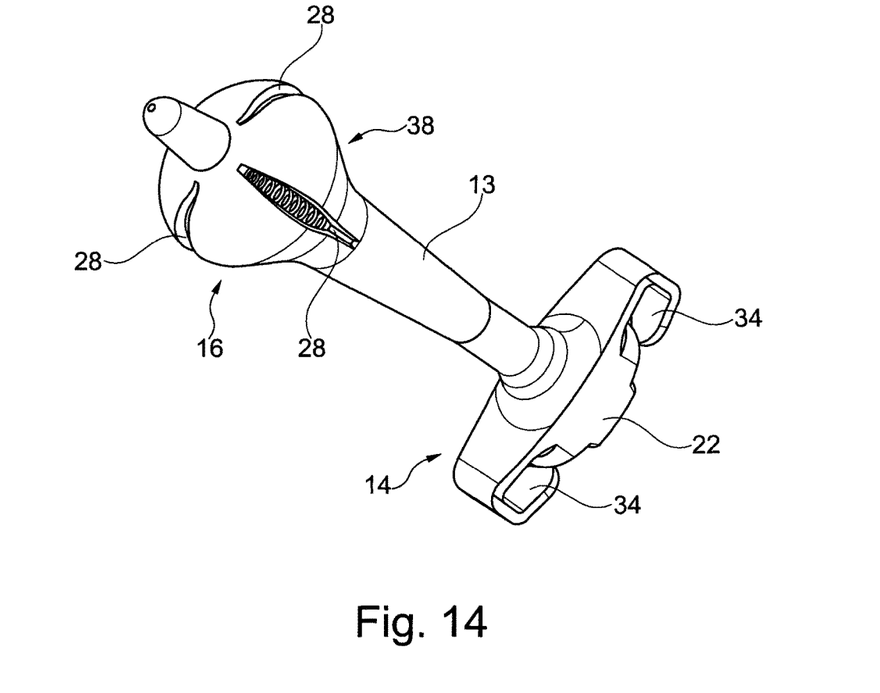

FIGS. 13 and 14 are schematic perspective views of an incontinence device as described above. The incontinence device illustrated in FIGS. 13 and 14 includes four slits 28 or openings to be placed inside the bladder of a user. Urine is allowed to pass though these slits 28. In other embodiments the number of slits or openings may be different for various reasons. The number of slits or openings may vary from one, two, three, four, five, six or more. The number of slits or openings may depend on the size of each opening and the overall strength of the second end of the device. The individual slits need not be identical or similar, e.g. in an embodiment with four slits, two may be relatively large and the other two may be relatively smaller. It should be clear that also other geometries of the openings will work fine, e.g. circular or elliptical apertures.

The head part includes one or two lips or tabs 34 that the user may pull as described above so as to discharge urine from the bladder. Alternatively, or in combination herewith an external magnetic device may be used, as described above, to move the valve member inside, not visible in these figures. The body of the device has a tapering geometry so as to provide a surface abutting the inner wall of the urethra.

The enlarged end 38 provides an increased diameter of the device for the part inside the bladder, or at the part of the urethra that widens and becomes the inner wall of the bladder.

FIG. 15 is a perspective sectional view of an embodiment of the invention, wherein a magnetic element or device 40 is used to open the valve, i.e. to displace the valve member 26 axially along the length of the flow control device 10 (along longitudinal axis X) to a second position away from a first position abutting the valve seal surface 23, allowing urine to flow along inside of coil 21 and through passage P. The valve member 26 is shown as a ball 26 resting in the first position against a peripheral surface 23 defining the valve seal surface. In the aforementioned second position the ball 26 rests against a peripheral surface 31 having cut-away portions along the periphery defining together the passage P such that fluid may exit even when the ball 26 rests against the surface 31. Operation of the valve member 26 is in principle as discussed in connection with FIG. 12: the valve member 26 is a magnet and is biased to its first, closing position by magnetic attraction to the metal coil 21. The magnetic field of the magnetic element 40 is stronger than that provided by the valve member 26 such that the valve member 26 is drawn away from the valve seal surface 23. It is noted that the tool 20 shown in the drawings may be configured to seal against the peripheral surface 31 of the device 10 with only the passage P being open; where the device 10 is used by a person having problems emptying her bladder this means that there will be some resistance to outflow of urine through opening 15 when it still remains for the user to withdraw the tool 20, i.e. where the valve body 26 still does not rest against the valve seal surface in its first, sealing position.

Figure 16:
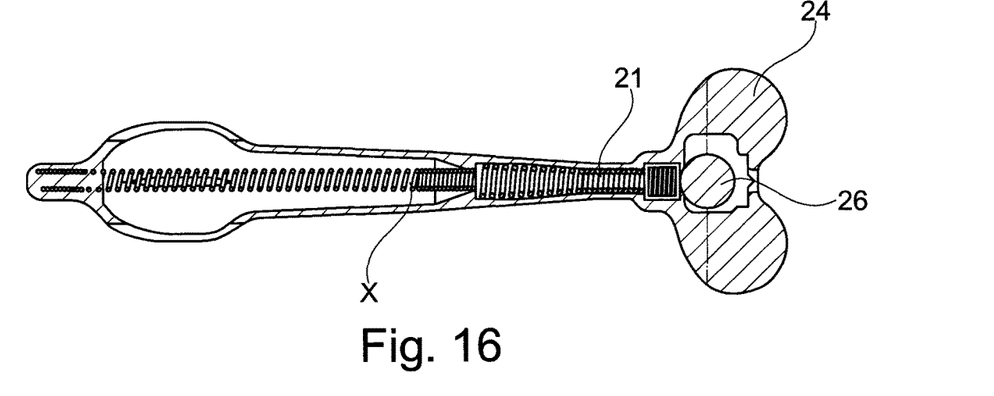
Figure 17:
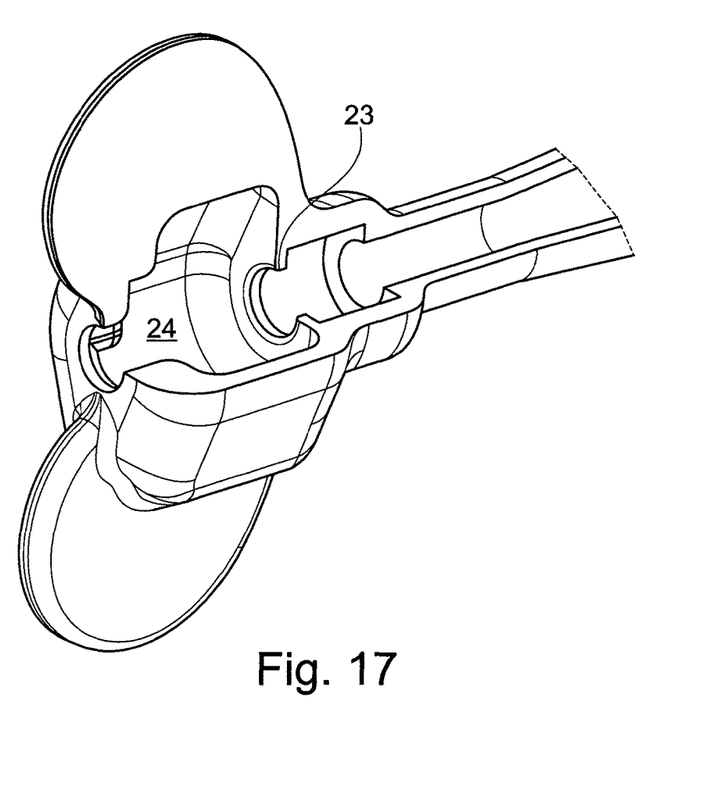

While in the embodiments of FIGS. 1-14 the chamber 24 of the head part 22 wherein the valve member 26 is displaceable is shown as allowing the valve member 26 to be displaced to either side of the longitudinal axis X it will be understood that any design of the chamber 26 allowing the valve member to be displaced sideways out of the path of the mounting tool 20 and away from the valve seat may be contemplated. Such a solution is shown in FIG. 16 where the ball-shaped valve member 26 is displaceable to one side of the axis X only, and being held in the shown position after removal of the tool 20 by magnetic attraction between the coil 21 of the metal valve member 26. Drawing the valve member 26 away from the valve seat 23 may be done by holding a magnetic device 40 as shown in FIG. 12 next to the side of the device 10 at its first end 14, or by holding the magnetic device 40 aligned with the axis X, as shown in FIG. 15 which gives rise to an axial displacement of the valve member 26.

It is noted that the device may be removed by the user manually pulling the device out of the urethra, the second end flexing and changing shape to allow for the removal.

Presently preferred materials for the device include silicone having a Shore value in the range 20-90, such as Wacker Chemicals Silpuran 6600, Shore 50, or MED4930/4920 manufactured by NuSil Inc. The coil may be made from Sandvik Bioline 7C27 or any magnetically attractive material, preferably with a coating for corrosion protection. Other biocompatible, elastic materials may be used.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A urine flow control device for insertion into a urethra, the device comprising:
    a hollow body having a first end, an opposite second end, and a middle part connecting the first end and the second end, wherein the first end, the second end, and the middle part define a hollow body chamber, the body being extensible along a longitudinal axis, the body having a diameter dimensioned to fit within the urethra;
    a fluid channel defined between the first end and the second end within the hollow body chamber;
    a head part at the first end of the body, the head part comprising a head chamber containing a displaceable valve member and a valve sealing surface, the displaceable valve member being configured to seat against the valve sealing surface to seal the fluid channel, the head part having an opening communicating with the hollow body chamber through the head chamber and the valve sealing surface; and
    a mounting tool configured for insertion into the hollow body chamber through the opening, the head chamber, and the valve sealing surface, the mounting tool being further configured to extend the body along the longitudinal axis when the mounting tool engages the second end of the body from the hollow body chamber;
    wherein the displaceable valve member is configured to be displaced from the valve sealing surface by the insertion of the mounting tool into the head chamber through the opening; and
    wherein the head part includes a gripping portion having a dimension transverse to the longitudinal axis that is sufficiently greater than the diameter of the body to prevent the head part from entering the urethra when the body is installed in the urethra, and wherein the gripping portion includes at least two radially-extending gripping tabs, each of which extends distally from the head part.

2. The urine flow control device of claim 1, wherein the valve member is sideways displaceable within the head chamber between a first position sealing the hollow body chamber after removal of the mounting tool, and a second position allowing fluid to flow through the opening.

3. The urine flow control device according to claim 2, wherein the valve member is biased towards the first position from the second position.

4. The urine flow control device according to claim 3, wherein valve member is biased towards the first position through magnetic attraction.

5. The urine flow control device according to claim 3, wherein the valve member is biased towards the first position by a force arising through deformation of the head part when the valve member is in the second position.

6. The urine flow control device according to claim 1, wherein the valve member is displaceable along the longitudinal axis, from a first position seated against the valve sealing surface to a second position displaced from the valve sealing surface.

7. The urine flow control device according to claim 1, wherein the mounting tool is movable along the longitudinal axis, and wherein the valve member is sideways displaceable within the head chamber between a first position sealing the hollow body chamber and a second position displaced from the longitudinal axis.

8. The urine flow control device according to claim 1, wherein the valve member is ball shaped.

9. The urine flow control device according to claim 1, wherein the mounting tool is elongated, with a proximal end and a distal end, the distal end being engageable with the second end of the body.

10. The urine flow control device according to claim 1, wherein the body has a well at the second end.

11. The urine flow control device according to claim 10, wherein the well is configured for receiving the distal end of the mounting tool.

12. The urine flow control device according to claim 1, further comprising a helical coil extending longitudinally through the hollow body chamber between the valve sealing surface and the second end of the body, the helical coil being of a magnetically attractive material.

13. The urine flow control device according to claim 12, wherein the helical coil includes a part having an increased coil diameter, and wherein the part having an increased coil diameter is received in a recess in the head chamber.

14. The urine flow control device according to claim 12, wherein the helical coil has a first pitch inside the hollow body chamber and a second pitch inside the head chamber, wherein the second pitch is greater than the first pitch.

15. The urine flow control device according to claim 12, wherein the body has a well at the second end, and wherein the helical coil is received in the well together with the mounting tool.

16. The urine flow control device according to claim 1, wherein the body has a tapering outer geometry.

17. The urine flow control device according to claim 1, wherein the second end of the body comprises a protrusion configured for engaging the inner wall of a bladder or the urethra when the body is inserted in the urethra.

18. The urine flow control device according to claim 17, wherein the mounting tool, when positioned in the hollow body chamber, extends the length of the body and reduces the diameter of the protrusion when pushed longitudinally to engage the second end of the body.

19. The urine flow control device according to claim 1, further comprising a rigid member embedded in the body at the first end so that the opening maintains a specific geometry when abutted by the valve member.

20. The urine flow control device according to claim 19, wherein the rigid member comprises a magnetic metal.

21. The urine flow control device according to claim 1, wherein the body is integral with the head part.

22. The urine flow control device according to claim 1, wherein the body is formed from one of silicone and polyurethane.

23. The urine flow control device according to claim 1, wherein the gripping portion is configured to be pulled so as to deform the head part, whereby the deformation of the head part allows urine pressure to displace the valve member from the valve sealing surface without the insertion of the mounting tool into the hollow body chamber.

24. The urine flow control device according to claim 1, further comprising an anti-bacterial coating on an outer surface of the body.

25. The urine flow control device according to claim 1, wherein the valve member comprises a coating layer that performs at least one function selected from the group consisting of reducing corrosion, reducing deposits, facilitating cleaning, and improving biocompatibility.

* * * * *